United States Patent
McAlexander et al.

(10) Patent No.: US 7,959,554 B2
(45) Date of Patent: Jun. 14, 2011

(54) MEDICAL GRAFT PRODUCTS WITH DIFFERING REGIONS AND METHODS AND SYSTEMS FOR PRODUCING THE SAME

(75) Inventors: Chad S. McAlexander, Delphi, IN (US); Clay Fette, Palm Beach Gardens, FL (US); Jason P. Hodde, West Lafayette, IN (US); Matthew R. Graham, Fort Wayne, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 997 days.

(21) Appl. No.: 11/523,450

(22) Filed: Sep. 19, 2006
(Under 37 CFR 1.47)

(65) Prior Publication Data
US 2007/0166395 A1    Jul. 19, 2007

Related U.S. Application Data

(63) Continuation of application No. PCT/US2005/010720, filed on Mar. 29, 2005.

(60) Provisional application No. 60/628,006, filed on Nov. 15, 2004, provisional application No. 60/557,248, filed on Mar. 29, 2004.

(51) Int. Cl.
*A61F 2/04* (2006.01)

(52) U.S. Cl. ............... 600/37; 623/23.66; 623/23.72; 623/901; 623/917

(58) Field of Classification Search .......... 600/29–32, 600/37
See application file for complete search history.

(56) References Cited

U.S. PATENT DOCUMENTS

| | | | |
|---|---|---|---|
| 4,218,782 A |   | 8/1980 | Ryagg |
| 4,585,458 A | * | 4/1986 | Kurland ............... 623/13.17 |
| 4,902,508 A |   | 2/1990 | Badylak et al. |
| 4,956,178 A |   | 9/1990 | Badylak et al. |
| 5,061,245 A |   | 10/1991 | Waldvogel et al. |
| 5,156,620 A |   | 10/1992 | Pigott |
| 5,281,422 A |   | 1/1994 | Badylak et al. |
| 5,411,552 A |   | 5/1995 | Andersen et al. |
| 5,554,389 A |   | 9/1996 | Badylak et al. |
| 5,607,465 A |   | 3/1997 | Camilli |
| 5,609,598 A |   | 3/1997 | Laufer et al. |
| 5,720,776 A |   | 2/1998 | Chuter et al. |
| 5,755,791 A |   | 5/1998 | Whitson et al. |

(Continued)

FOREIGN PATENT DOCUMENTS
EP    1543798 A2    6/2005
(Continued)

OTHER PUBLICATIONS

Gorisch et al., "Heat Induced Contraction of Blood Vessels", Lasers in Surgery and Medicine, 1982, vol. 2, No. 1, pp. 1-13. Wiley-Liss, United States.

(Continued)

*Primary Examiner* — Charles A Marmor, II
*Assistant Examiner* — Carrie Dorna
(74) *Attorney, Agent, or Firm* — Woodard, Emhardt, Moriarty, McNett & Henry LLP

(57) ABSTRACT

Described are methods and systems for drying remodelable materials, such that selective regions of the remodelable materials have differing properties. Also described are medical graft products having selective regions of differing material properties. Advantageous remodelable materials include collagenous extracellular matrix material, such as small intestine submucosa.

17 Claims, 5 Drawing Sheets

U.S. PATENT DOCUMENTS

| | | |
|---|---|---|
| 5,800,537 A | 9/1998 | Bell |
| 5,810,847 A | 9/1998 | Laufer et al. |
| 5,955,110 A | 9/1999 | Patel et al. |
| 5,993,844 A | 11/1999 | Abraham et al. |
| 5,997,575 A | 12/1999 | Whitson et al. |
| 6,014,589 A | 1/2000 | Farley et al. |
| 6,033,398 A | 3/2000 | Farley et al. |
| 6,036,687 A | 3/2000 | Laufer et al. |
| 6,071,277 A | 6/2000 | Farley et al. |
| 6,099,567 A | 8/2000 | Badylak et al. |
| 6,110,201 A | 8/2000 | Quijano et al. |
| 6,126,686 A | 10/2000 | Badylak et al. |
| 6,152,899 A | 11/2000 | Farley et al. |
| 6,165,172 A | 12/2000 | Farley et al. |
| 6,168,614 B1 | 1/2001 | Andersen et al. |
| 6,179,832 B1 | 1/2001 | Jones et al. |
| 6,200,312 B1 | 3/2001 | Zikorus et al. |
| 6,200,336 B1 | 3/2001 | Pavcnik et al. |
| 6,206,931 B1 | 3/2001 | Cook et al. |
| 6,287,334 B1 | 9/2001 | Moll et al. |
| 6,299,637 B1 | 10/2001 | Shaolian et al. |
| 6,475,232 B1 | 11/2002 | Babbs et al. |
| 6,508,833 B2 | 1/2003 | Pavcnik et al. |
| 6,530,956 B1 | 3/2003 | Mansmann |
| 6,582,462 B1 | 6/2003 | Andersen et al. |
| 6,666,892 B2 | 12/2003 | Hiles et al. |
| 6,716,241 B2 | 4/2004 | Wilder et al. |
| 6,752,828 B2 | 6/2004 | Thornton |
| 2001/0011187 A1 | 8/2001 | Pavcnik et al. |
| 2001/0039450 A1 | 11/2001 | Pavcnik et al. |
| 2002/0103542 A1* | 8/2002 | Bilbo ............ 623/23.72 |
| 2002/0123800 A1 | 9/2002 | Taheri |
| 2002/0188348 A1 | 12/2002 | DiMatteo et al. |
| 2003/0036795 A1 | 2/2003 | Andersent et al. |
| 2003/0130726 A1 | 7/2003 | Thorpe et al. |
| 2003/0191525 A1 | 10/2003 | Thornton |
| 2003/0208261 A1 | 11/2003 | Thorpe et al. |
| 2004/0006353 A1 | 1/2004 | Bosley, Jr. et al. |
| 2004/0015230 A1 | 1/2004 | Moll et al. |
| 2004/0039246 A1* | 2/2004 | Gellman et al. ............ 600/30 |
| 2004/0049262 A1 | 3/2004 | Obermiller et al. |
| 2004/0193253 A1 | 9/2004 | Thorpe et al. |

FOREIGN PATENT DOCUMENTS

| | | |
|---|---|---|
| EP | 1648347 | 4/2006 |
| GB | 2423934 A | 9/2006 |
| GB | 2432845 A | 6/2007 |
| WO | WO 94/17841 A1 | 8/1994 |
| WO | WO 97/37614 A1 | 10/1997 |
| WO | WO 99/19005 A1 | 4/1999 |
| WO | WO 00/32112 A1 | 6/2000 |
| WO | WO 00/45691 | 8/2000 |
| WO | WO 01/19285 | 3/2001 |
| WO | WO 01/70091 | 9/2001 |
| WO | WO 03/002168 | 1/2003 |
| WO | WO 03/009764 | 2/2003 |
| WO | WO 03/043506 | 5/2003 |
| WO | WO 03/070124 | 8/2003 |
| WO | WO 03/092546 | 11/2003 |

OTHER PUBLICATIONS

Luo, J. et al., "Direct Intrahepatic Portacaval Shunt: An Experimental Study", World Journal of Gastroenterology, Feb. 2003, vol. 9, No. 2, pp. 324-328. The WJG Press, China.

Min, R.J. et al., "Endovenous Laser Treatment of Saphenous Vein Reflux: Long-Term Results", Journal of Vascular and Interventional Radiology, Aug. 2003, vol. 14, No. 8, pp. 991-996. Society of Cardiovascular and Interventional Radiology, United States.

* cited by examiner

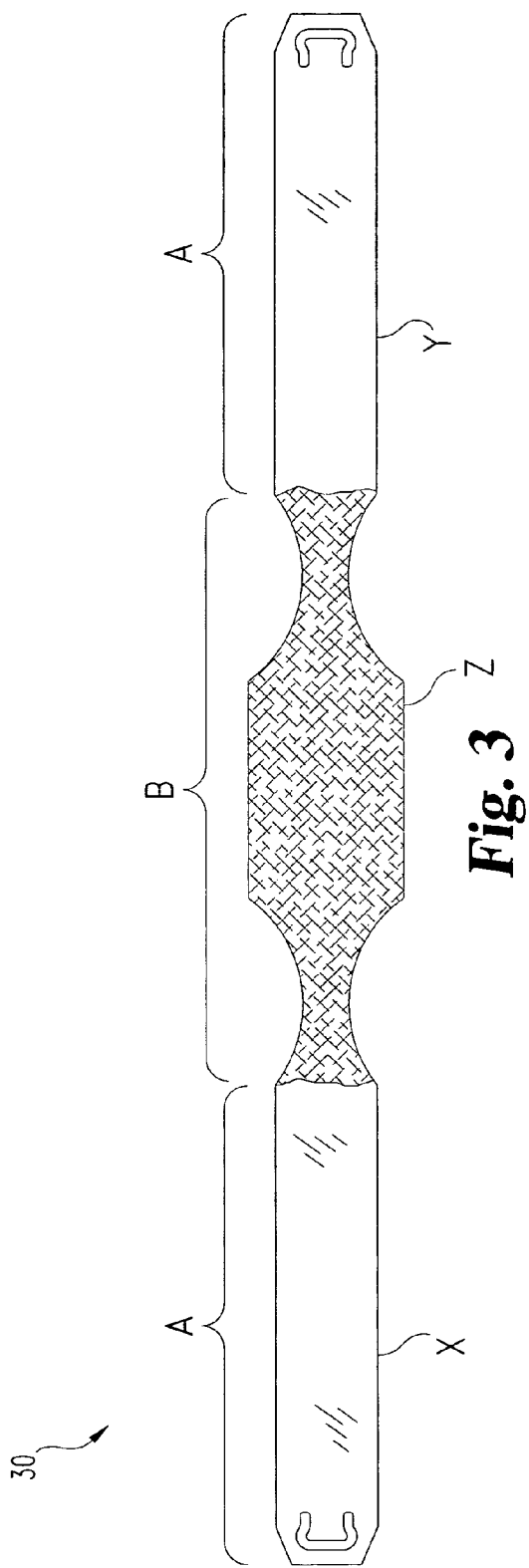
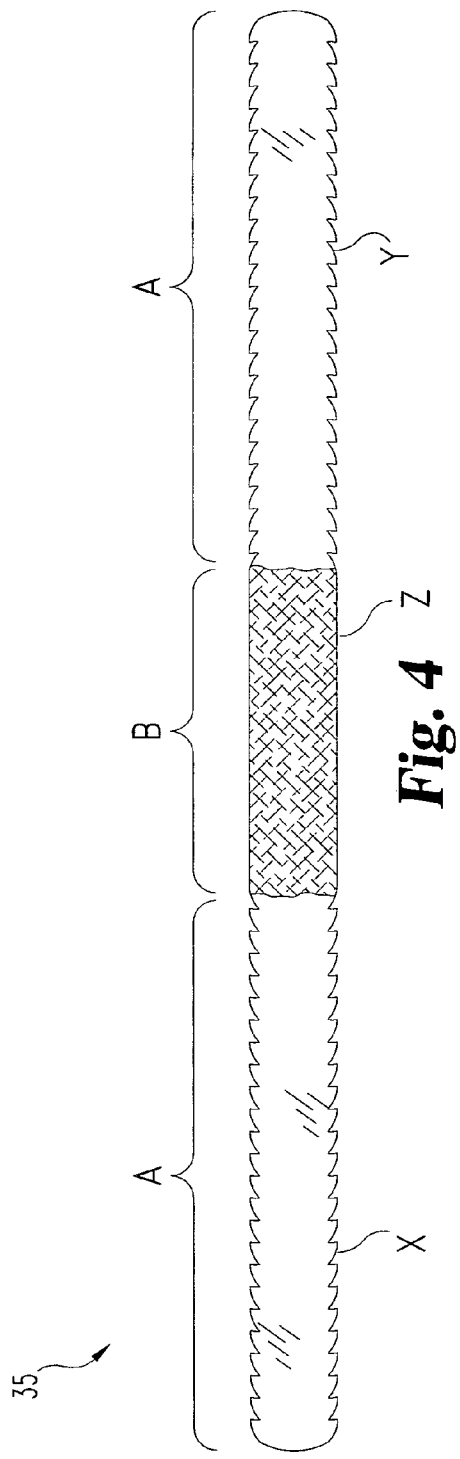

MEDICAL GRAFT PRODUCTS WITH DIFFERING REGIONS AND METHODS AND SYSTEMS FOR PRODUCING THE SAME

STATEMENT OF RELATED APPLICATIONS

This application is a continuation of International Application No. PCT/US2005/010720 filed Mar. 29, 2005 (which was published in English), which claims the benefit of U.S. Provisional Patent Application Ser. No. 60/628,006 filed Nov. 15, 2004 and U.S. Provisional Patent Application Ser. No. 60/557,248 filed Mar. 29, 2004, all of which are incorporated herein by reference in their entirety.

BACKGROUND

The present invention relates generally to remodelable medical graft products, including multilaminate medical graft products, having two or more regions providing differential properties, for example differential porosity and/or ingrowth of patient tissue. The invention also provides methods and systems for differentially drying remodelable materials that include vacuum drying a frozen, partially compressed and/or covered remodelable material.

As further background, extracellular matrix materials, including submucosa, are known medical graft materials. Submucosa from various biological structures such as small intestine, stomach, and the urinary bladder provide predominantly collagenous materials useful in a variety of surgical procedures where tissue support and/or ingrowth are desired. As one example, sheet-form submucosa material has been suggested and used as a surgical graft for tissue support, e.g. in hernia repair. Portions or all of the graft may include a multiple layer configuration to provide strength or reinforcement.

Often times, it is desirable to dry a medical graft product. Graft products may be dried for many reasons, such as to fuse graft material together, or for more effective storage of the sterile graft product. Several drying methods are known in the art, including lyophilization, air drying, and vacuum pressing. Drying by evaporation, or air drying, generally comprises drying a partially or completely hydrated remodelable material by allowing hydrant to evaporate from the material. Vacuum pressing generally comprises compressing a fully or partially hydrated remodelable material while the material is subject to a vacuum. Lyophilization generally includes drying a frozen material under a vacuum.

There remain needs for improved or alternative remodelable graft materials with beneficial material properties and tissue response, as well as methods and systems for making and using those materials. The present invention is addressed to these needs.

SUMMARY OF INVENTION

In one aspect, the invention relates to methods for preparing dried extracellular matrix (ECM) medical graft products. The methods include drying a frozen remodelable material under a vacuum while portions of the material are shielded, e.g. covered and/or compressed.

In another aspect, the invention provides a drying method involving drying a frozen remodelable ECM material under a vacuum while heating selective portions of the material.

In yet another aspect, the invention provides a remodelable medical graft product having selected regions with different material properties. Advantageous such remodelable materials include ECM material, such as mammalian small intestine submucosa.

In still yet another aspect, the invention provides a layered medical graft construct, where portions of the layers are compression bonded to one another, thereby leaving the matrix structure in those portions collapsed, while leaving the matrix structure in the remaining areas open.

In yet another aspect, the invention provides a method for making a medical graft product that includes lyophilizing a hydrated ECM material, wherein regions of at least one surface of the material are shielded during lyophilization. In certain embodiments, lyophilization includes creating a vacuum around a hydrated ECM construct.

The present invention provides improved and/or alternative methods and systems for drying remodelable materials, as well as improved and/or alternative medical graft products. Additional embodiments and features and advantages of the invention will be apparent from the descriptions herein.

BRIEF DESCRIPTION OF THE DRAWINGS

FIG. 3 depicts a urethral sling according to one embodiment of the present invention.

FIG. 4 depicts a urethral sling according to one embodiment of the present invention.

DETAILED DESCRIPTION

Figure 1:
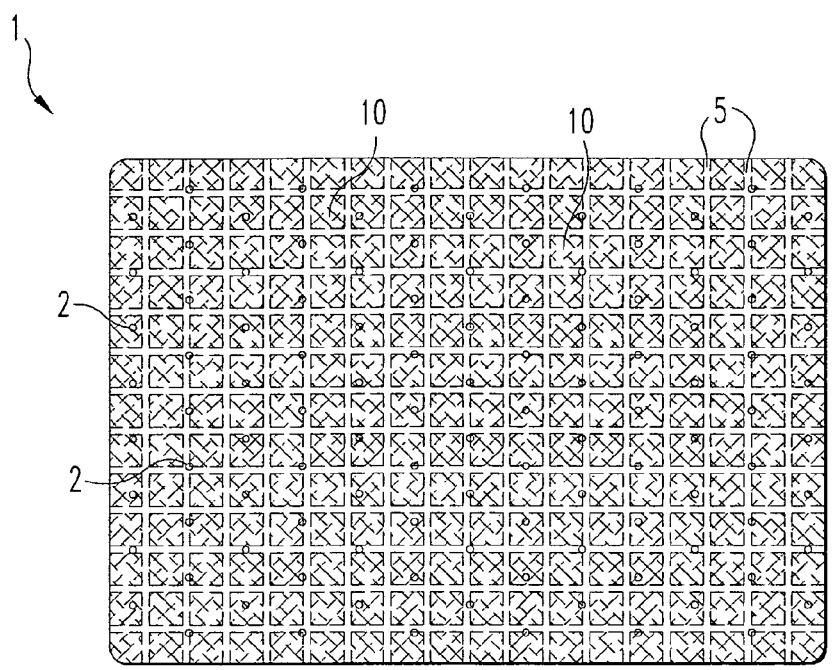
FIG. 1 depicts a hernia graft product according to one embodiment of the present invention.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, the present invention provides a medical graft product that includes a remodelable ECM material having at least two regions that provide properties, such as differing porosity, stiffness, and/or propensity to promote growth of patient tissue into the remodelable material. The invention also provides differential drying methods for remodelable ECM materials that include vacuum drying a frozen, partially compressed and/or covered remodelable material.

Turning now to a discussion of graft materials, the remodelable materials of the invention can include collagenous extracellular matrix (ECM) material, such as submucosa, renal capsule membrane, dura mater, pericardium, serosa, peritoneum, or basement membrane. The preferred medical graft products of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in the present invention, and its isolation and treatment, reference can be made, for example, to U.S. Pat. Nos. 4,902,508, 5,554, 389, 5,993,844, 6,206,931, and 6,099,567.

As prepared, the extracellular matrix material may optionally retain growth factors or other bioactive components native to the source tissue. For example, the matrix material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material of the invention may include other biological materials such as heparin, heparin sulfate, hyaluronic acid, fibronectin and the like. Thus, generally speaking, the ECM material may include a bioactive component that induces, directly or indirectly, a cellular response such as a change in cell morphology, proliferation, growth, protein or gene expression. Further, in addition or as an alternative to the inclusion of such native bioactive components, non-native bioactive components such as those synthetically produced by recombinant technology or other methods, may be incorporated into the ECM material.

ECM material used in the invention is preferably highly purified, for example, as described in U.S. Pat. No. 6,206,931. Thus, preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plate forming units (PFU) per gram, more preferably less than about 5 PFU per gram. The ECM material used in the invention is preferably disinfected with an oxidizing agent, particularly a peracid, such as peracetic acid. These and additional properties of submucosa taught in U.S. Pat. No. 6,206,931 may be characteristic of the ECM material used in the present invention.

In certain inventive embodiments, an ECM-based remodelable material comprises a multilaminate ECM material. Illustrative such multilaminate ECM materials can include from one to about ten or more layered ECM segments formed into a variety of different shapes and sizes. For example, in one embodiment, a multilaminate ECM material can include a plurality of individual ECM segments, for example arranged and layered in a partially or completely overlapping manner such as a crisscross and/or crosshatch or other suitable arrangement or pattern. Alternatively, a multilaminate ECM material can include a single ECM segment that is folded or loosely rolled over itself one or more times. Still alternatively, a multilaminate ECM material can include one or more smaller ECM segments, or bands, placed in the fold of a larger ECM segment, or alternatively, between two or more larger, layered ECM segments. For additional information as to multilaminate ECM constructs, reference can be made to U.S. Pat. Nos. 5,755,791, 5,955,110, and/or 5,997, 575.

Optionally, in other inventive embodiments, the multilaminate remodelable material can further comprise a plurality of perforations or bores that may extend through the entire multilaminate construct, or alternatively, form a cavity within the construct that extends only part way through the construct. The spacing, size, shape, and depth of the penetrations can vary. For additional information as to ECM construct perforations, reference can be made to U.S. Pat. No. 5,755,791.

Optionally, an adhesive, glue, or any other bonding agent may be placed between ECM layers to achieve a partial or complete bond. Suitable bonding agents may include, for example, collagen gels or pastes, gelatin, or other agents including reactive monomers or polymers, such as cyanoacrylate adhesives for example. As well, bonding can be facilitated using chemical cross-linking agents, such as glutaraldehyde, formaldehyde, epoxides, genipin or derivatives thereof, carbodiimide compounds, polyepoxide compounds, or other similar agents. Cross-linking of ECM materials may also be catalyzed by exposing the matrix to UV radiation, by treating the collagen-based matrix with enzymes such as transglutaminase and lysyl oxidase, and by photocrosslinking. Additionally, bonding may be achieved by combining any two or more of the above bonding agents or methods.

Turning now to a discussion of drying methods known in the art, drying a remodelable material by lyophilization can include hydrating the remodelable material, so as to fill the voids in the material matrix with a hydrant. The hydrant can comprise any suitable hydrant known in the art, such as purified water or sterile saline, or any suitable combination thereof. Next, the hydrated material can be placed in a freezer until the material and hydrant are substantially in a frozen or solid state. Thereafter, the frozen material and hydrant can be placed in a vacuum chamber and a vacuum is initiated. Once at a sufficient vacuum, as is known in the art, the frozen hydrant will sublime from the material, thereby resulting in a dry remodelable material. Alternatively, the graft material can be lyophilized without a pre-freezing step, wherein a strong vacuum is applied to the hydrated material to result in evaporative cooling which both freezes and dries the material. Desirably, a remodelable material is able to maintain a substantial amount of void space, or open area, that exists in its matrix structure throughout the lyophilization process.

Additionally, in instances when a hydrated ECM material is lyophilized without a pre-freezing step, the ECM material is able maintain an open matrix structure throughout the drying process. The open matrix structure is maintained, in part, due to the evaporative thermodynamics that occur as a vacuum is created around the hydrated ECM material. As the vacuum is pulled, the liquid hydrant, which is dispersed throughout the ECM material, starts to evaporate, which, in turn, causes at least a portion of the remaining liquid hydrant to freeze. After the phase change to solid state occurs, the solid hydrant sublimes from the ECM material as the material dries. This phase change of hydrant from liquid to solid state during lyophilization enhances the ability of the ECM material to occupy an open matrix structure after drying is complete.

Drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. Unlike lyophilization, the amount of open area or voids in a material's matrix structure is diminished during evaporative drying.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

Turning now to a discussion of material properties, remodelable materials having an open matrix structure exhibit some different material properties than remodelable materials having a more diminished or collapsed matrix structure. For example, a material having an open matrix structure is soft and readily compliant to an implant site. In contrast, a material having a more collapsed matrix tends to be more stiff or rigid, more durable, and have greater compliance, or shape memory than a material with a more open matrix structure.

Additionally, the rate and amount of tissue growth in and/or around a remodelable material are controlled by several factors. One such factor includes the amount of open space available in the material's matrix structure for the infusion and support of a patient's cell building components, such as fibroblasts. Therefore, an open matrix structure provides for quicker, and sometimes more, growth of patient tissue in the remodelable material. This increased rate of patient tissue growth in the remodelable material can lead to quicker remodeling of the material by patient tissue.

Turning now to a discussion of drying methods of the invention, in one aspect, the differential drying method generally comprises drying a remodelable material, under vacuum, wherein a portion of the material contains a frozen hydrant, while other regions of the material contain hydrant in liquid form, or alternatively, frozen hydrant that is converted to liquid form during the drying process. Any suitable method or device may be used to control the physical state of hydrant in the remodelable material during drying, such as, for example, a temperature control device, or, use of thermodynamic means, such as covering or shielding a portion of the material subject to vacuum, with a suitable shielding material, such as a material of sufficient porosity to induce differential drying.

Further, the remodelable material dried according to any one of the aspects of the invention will comprise at least two regions having differing properties. These differing regions can be established in certain specific locations or comprise a certain arrangement or pattern within the remodelable material. This arrangement or pattern can be selected in order to promote or achieve any one of a number of desirable results, such as, for example, enhancing bonding of layers within the remodelable material, differing the rate and/or ability of patient tissue to infiltrate or invade the remodelable material, increasing the compliance and/or durability of the remodelable material, and/or forming the remodelable material or a portion of the remodelable material to match certain anatomical structures, such as nerves or tendons. Additionally, the arrangement or pattern can be selected to promote or achieve combinations of any of the previous desirable results.

In accordance with one aspect of the invention, differential drying includes first hydrating a remodelable material, such as a multilaminate remodelable material, for example, with any suitable fluid known in the art, or any suitable combination thereof. Next, one or more regions of the hydrated material are compressed with any suitable press or pressing device, such as one or more plastic or metal segments, or an aggregation of such segments formed into a lattice type structure. In one embodiment, compressive blocks comprising suitable surface features can be pressed into the material. In this embodiment, the surface features are substantially non-porous while the remainder of the block is sufficiently porous to allow the non-compressed regions of the material to lyophilize through the block. Alternatively, in another embodiment, a screen, or other suitable lattice type structure, can be compressed between the material and a compressive block of suitable porosity.

Additionally, the lattice type structure can comprise any suitable geometric pattern, including a crisscross or crosshatch pattern, or a pattern comprising one or more elongate lines extending substantially across the surface of the graft. For example, the lattice type structure can be arranged so the resulting pattern in the material can comprise at least first and second intersecting elongate portions. Preferably, the resulting pattern comprises a plurality of such portions, forming bands or swaths across a portion of, if not the entire surface of the material. In certain embodiments, the bands or swaths can occupy a width of from about 0.2 mm to about 15 mm or more. In alternative embodiments, the bands can have a width of from about 0.5 mm to about 4 mm.

Thereafter, the hydrated material is frozen while maintaining the one or more regions in their compressed state. After freezing is substantially complete, the frozen material, with one or more regions remaining under compression, is placed in a rigid vacuum chamber and the chamber is evacuated. As the vacuum deepens, the frozen hydrant in the uncompressed, and uncovered portions of the frozen material sublimes, causing those portions of the material to dry by lyophilization. While the uncovered portions of the material are lyophilizing, the covered and compressed regions dry by a combination of evaporative drying and vacuum pressing. This differential drying method results in a remodelable material having a somewhat open matrix structure in the lyophilized areas, while having a more diminished or collapsed matrix structure in the regions dried by vacuum pressing and evaporative cooling.

In accordance with another aspect of the invention, differential drying includes first hydrating a remodelable material with a suitable hydrant or combination of hydrants. Next, at least one region of the material is covered with a suitable covering material, such as a substantially non-porous material, for example. Suitable covering materials can include various metals, such as stainless steel, as well as polymers, such as polyethylene (e.g., TYVEK®, polytetrafluoroethylene (PTFE) (e.g., TEFLON®, or an acetyl resin (e.g., DELRIN®), or a suitable fabric. After covering or shielding is complete, the hydrated material is sufficiently frozen. Optionally, the covering material can be located on the remodelable material after the hydrated material is frozen. Thereafter, the remodelable material, with covered regions, is placed in a vacuum chamber having rigid walls. As the vacuum is formed, the uncovered portions of the material dry by lyophilization, while the covered regions dry by evaporative cooling. This differential drying method results in a remodelable material having a somewhat open matrix structure in the lyophilized areas, while having a more diminished or collapsed matrix structure in the regions dried by evaporative cooling.

In accordance with yet another aspect of the invention, differential drying includes hydrating and freezing a remodelable material. Thereafter, the frozen material is placed in a rigid vacuum chamber where it is subjected to heating devices capable of heating one or more regions of the remodelable material to maintain only the hydrant in those regions in substantially liquid form during drying. Such heating elements can include, for example, devices that contact the material, such as resistive or electrical heaters and/or non-contact devices, such as radiative heaters with apertures capable of targeting specific material regions. Next, a vacuum is formed in the chamber, and the portions of the material containing hydrant in a substantially solid state dry by lyophilization, while the heated regions of the material dry by evaporative cooling. This differential drying method results in a remodelable material having a somewhat open matrix structure in the lyophilized areas, while having a more diminished or collapsed matrix structure in the regions dried by evaporative cooling.

In accordance with yet another aspect of the invention, differential drying includes hydrating and freezing a remodelable material. Thereafter, the material can be placed in a vacuum chamber, where one side of the material is covered with a suitable covering material. As a vacuum is drawn, frozen hydrant sublimes through the uncovered side, while hydrant evaporates either from or through the covered side. Alternatively, in another embodiment, one side of the material can be temperature controlled during drying, such that the hydrant on that side liquefies before drying. These differential drying methods create a remodelable material having a somewhat open matrix structure on one side, while having a more diminished or collapsed matrix on the other side.

In certain embodiments, differential drying can include shielding portions or regions of a sufficiently hydrated ECM sheet or multilaminate material and thereafter providing a vacuum around the shielded material. The uncovered portions of the ECM material can dry via lyophilization under vacuum, as discussed above. The shielded regions can dry over time in these conditions as well. In these embodiments, the resulting ECM material can include a dry remodelable material having a somewhat open matrix structure that corresponds with the unshielded regions, while having a more diminished or collapsed matrix structure that corresponds to the shielded regions.

It is advantageous in some aspects of the invention to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention.

Turning now to a discussion of the medical graft products of the invention, the above materials and drying methods can be used to make medical graft constructs having advantageous properties. For example, in one embodiment, a differential drying method can be used to impart rigidity to one area of a medical graft, while leaving other areas flexible, such as, for example, by forming one or more ribs of collapsed or diminished matrix structure within a lyophilized ECM construct to aide in fixation of the construct within the patient. Alternatively, a drying method of the invention can be used to enhance the stiffness, or shape memory of a medical graft product, such as by forming ribs of collapsed matrix in an ECM construct, in a closed loop or other suitable shape for example, which can enhance the ability of the construct to open or occupy a predetermined shape once at the site of implantation. Still alternatively, in another embodiment, a drying method of the invention can be used to add rigidity and strength to certain sections, or all of a medical graft product. Yet still alternatively, in another embodiment, a drying method of the invention can be used to bond and/or compression bond the layers or segments, or portions of the layers or segments, of a multilaminate medical graft product together. For example, in one embodiment, a differential drying process of the invention can be used to bond at least two layers of a multilaminate medical graft construct. Selective regions of the construct can be compression bonded leaving the matrix structure in those regions in a substantially collapsed state, while the remaining regions of the construct can be bonded under non-compressive conditions, or compressive conditions that leave portions of the matrix structure open.

Additionally, in certain embodiments, ribs of collapsed or diminished matrix structure can be formed in an otherwise lyophilized ECM construct to match or correspond with the geometry of certain anatomical structures, such as nerves, blood vessels, ligaments, and/or tendons, for example. In these embodiments, the stiffened ribs can be advantageous in use, for example in facilitating the visualization of structures to enhance placement of the construct for fixation and/or to avoid certain anatomical structures or hazards.

In one embodiment, as shown in FIG. 1, a hernia repair graft 1 comprising an ECM material can be formed having a tight lattice pattern, where the lattice framework 5 dries by evaporative cooling and the framed portions 10 of the graft 1 dry by lyophilization. In this embodiment, as discussed above, the graft material can comprise multiple SIS or other ECM layers, such as four to eight layers, which bond together as the graft construct dries under vacuum. The more rigid, framework 5 sections in FIG. 1 add rigidity and cohesiveness to the graft structure, while the framed portions 10 serve to enhance the ingrowth of patient tissue into the graft.

Additionally, in the embodiment depicted in FIG. 1, the lattice is shown as a tight square pattern, wherein the width of each lattice band ranges from about 0.5 mm to about 2 mm. However, the lattice structure can comprise any suitable geometric pattern, including a crisscross or crosshatch pattern, or a pattern comprising elongate lines extending substantially across the surface of the graft.

Further, as shown in FIG. 1, the hernia graft construct may include perforations or bores 2. These pores may extend through the entire construct, or alternatively, form a cavity within the construct that extends only part way through the construct. The pores may be spaced in any suitable arrangement or pattern, variable or fixed, and may comprise any suitable size, shape, and/or depth.

Figure 2:
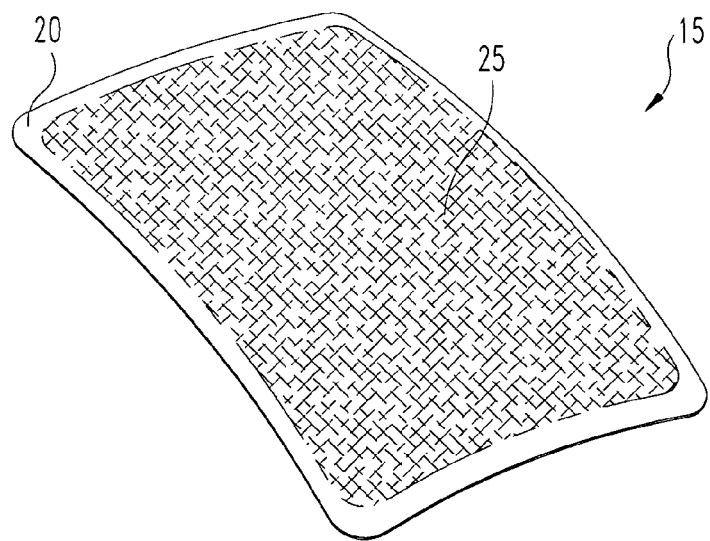
FIG. 2 is a perspective depiction of a hernia graft product according to one embodiment of the present invention.
Figure 5:
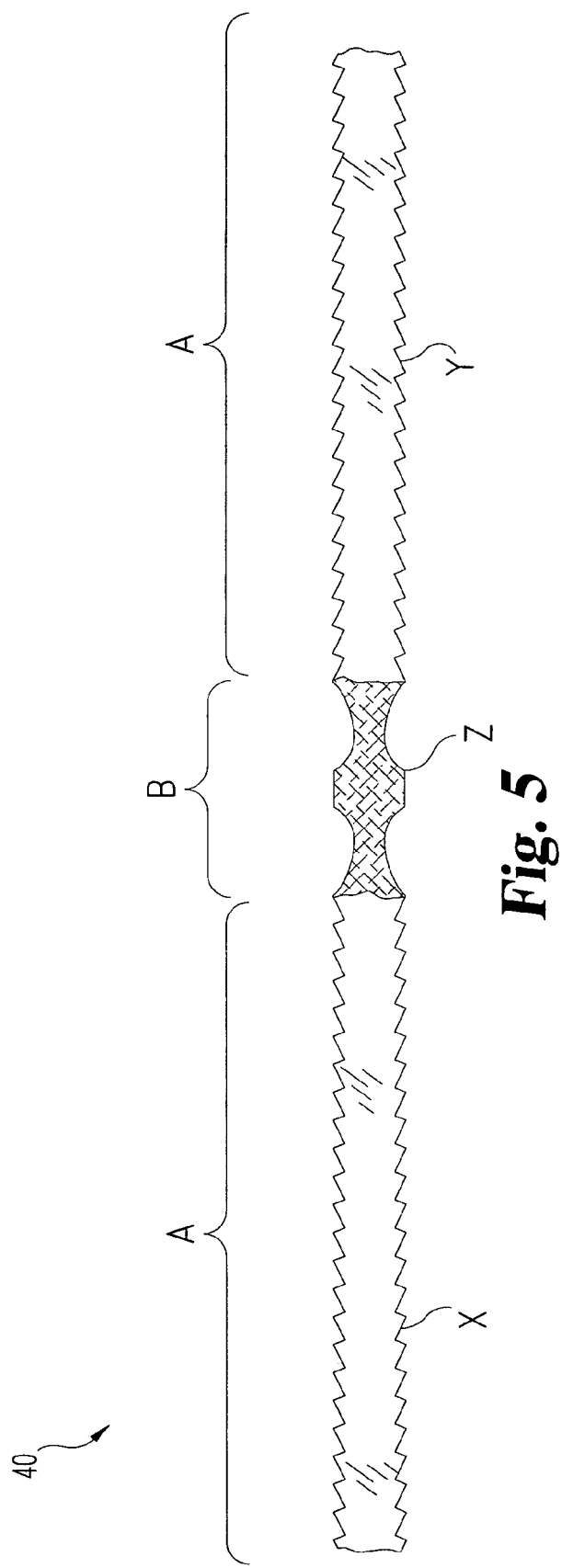
FIG. 5 depicts a urethral sling according to one embodiment of the present invention.
Figure 6:
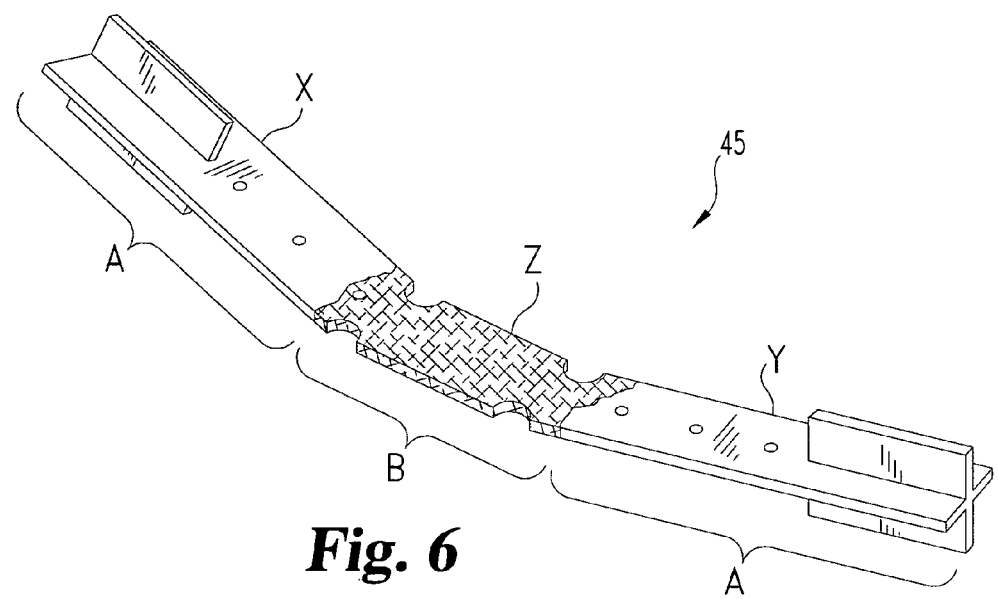
FIG. 6 is a perspective depiction of a urethral sling according to one embodiment of the present invention.
Figure 7:
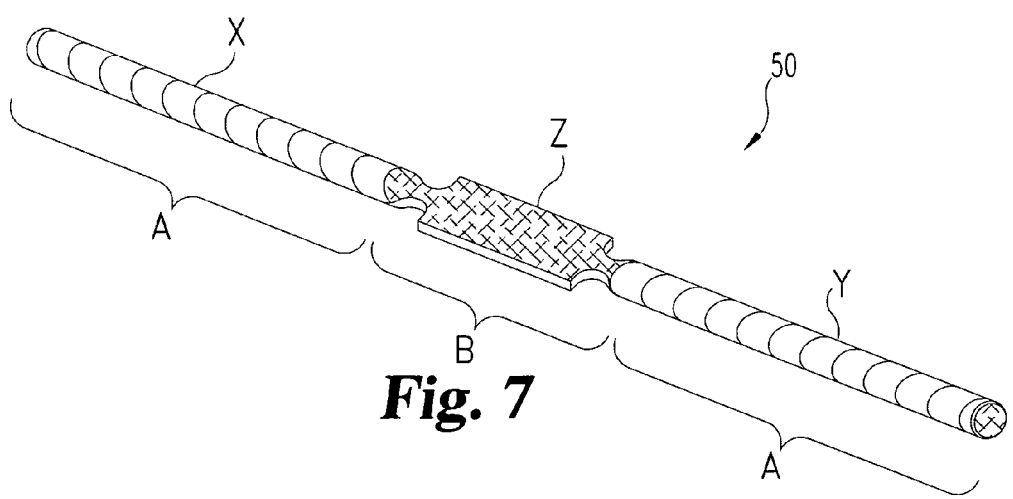
FIG. 7 depicts a urethral sling according to one embodiment of the present invention.

Turning now to FIG. 2, in an alternative embodiment, a hernia repair matrix 15 is depicted. The hernia graft of FIG. 2 is a multilaminate product comprising eight layers of ECM material, which are bonded together using a differential drying process of the invention. As displayed in FIG. 2, the hernia repair matrix has two differing regions 20, 25. The SIS or other ECM material in region 20 has a matrix structure that is in a diminished or collapsed state. The SIS or other ECM material in region 25 has a somewhat open matrix structure, similar to the matrix structure of freshly harvested SIS. The two regions in graft 15 provide a selective combination of differing properties, yielding a more functional graft product.

For example, the collapsed matrix structure imparts durability and rigidity to region 20, thereby enhancing its ability to receive and maintain sutures or staples. However, while region 20 is more suitable for receiving a fastening means, region 25 retains beneficial remodeling properties, thereby allowing quicker graft remodelability by patient tissue.

Turning now to FIGS. 3-7, shown are multiple embodiments of urethral slings 30, 35, 40, 45, 50 that can be made according to any one of the differential drying methods of the present invention. More detail on urethral slings can be found by reference to U.S. Pat. App. No 2004/0006353. The sling embodiments depicted in FIGS. 3-7 each comprise two arms X, Y for securing or anchoring the sling in a patient, and a central area Z for supporting the urethra. In each of the depicted sling embodiments, at least a portion of each arm X, Y has a somewhat diminished or collapsed matrix structure, and is translucent, as shown by area A. The center portion Z of each sling embodiment has an open matrix structure, which is relatively opaque, and is represented by area B.

Figure 8:
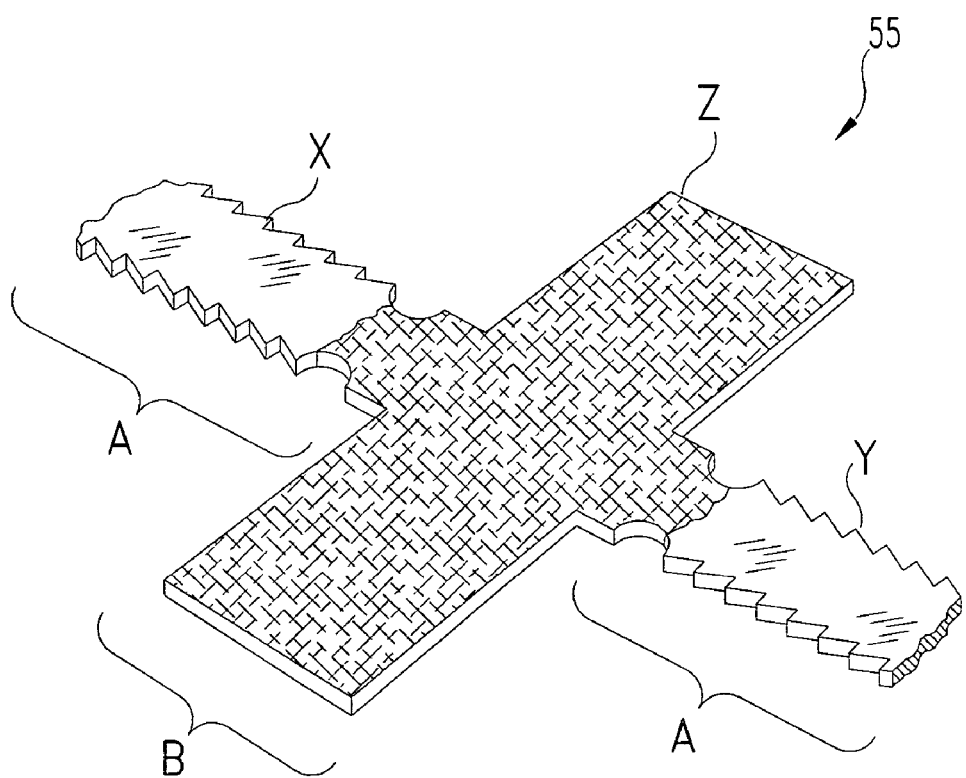
FIG. 8 is a perspective depiction of a urethra and bladder sling according to one embodiment of the present invention.

In another embodiment, as shown in FIG. 8, a differential drying method of the invention can be used to make the depicted bladder and urethral support or sling 55. More detail on bladder and urethral slings can be found by reference to U.S. Pat. App. No. 2004/0006353. The depicted embodiment 55 comprises two arms X, Y for securing or anchoring the sling in a patient, and a central area Z for supporting the urethra and bladder. At least a portion of each arm X, Y has a somewhat diminished or collapsed matrix structure, and is translucent, as shown by area A. The center portion Z of the sling has an open matrix structure, which is relatively opaque, and is represented by area B.

In each embodiment depicted in FIGS. 3-8, the differing matrix structures in areas A and B can be formed by any one of the differential drying methods discussed above. Further, the differing matrix structures impart rigidity to the sling arms X, Y while allowing the sling's center Z to remain flexible and compliant. The enhanced arm X, Y rigidity increases the anchoring capability of the sling, which desirably stabilizes the tension of the sling. Because the sling's center portion Z retains its flexibility, it more readily conforms to the urethra (FIGS. 3-7) or the urethra and bladder (FIG. 8), which reduces the possibility that the center portion Z will roll up and injure the urethra and/or bladder. Additionally, the center portion's Z open matrix provides for the relatively quick ingrowth of patient tissue.

As evident from the above discussions, in alternative embodiments, urethral and/or bladder slings can be produced using certain differential drying techniques of the invention such that the support region Z occupies a somewhat diminished or closed matrix structure, while at least a portion of each arm X, Y occupies a somewhat open matrix structure. In these embodiments, the support area Z will be more rigid than the lyophilized portions of each arm. This configuration can be desirable in instances where a relatively stiff construct is desirable to support the bladder and/or urethra while a more compliant or remodelable material is desirable to aide in securement of the sling within the patient.

The invention also encompasses medical products, such as a differentially dried hernia repair device of the invention sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly. The prosthesis device may be packaged wet or after it is dried.

All publications cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A medical graft product, comprising a multilaminate construct having two or more layers of remodelable collagenous extracellular matrix (ECM) material bonded to one another, the multilaminate construct having a first region in which the layers are bonded to one another during a drying method other than lyophilization and a second region in which the layers are bonded to one another during a lyophilization drying method, wherein the first bonded region comprises collagenous ECM material having a more collapsed matrix structure relative to the second bonded region, and wherein the second bonded region comprises lyophilized collagenous ECM material having a more open matrix structure than the first bonded region.

2. The product of claim 1, wherein the multilaminate construct has three or more layers.

3. The product of claim 1, wherein the first region and the second region are effective for promoting tissue of the patient to remodel the remodelable material.

4. The product of claim 1, wherein the first region comprises a lattice and the second region is framed by the lattice.

5. The product of claim 4, wherein the lattice has a square geometric configuration.

6. The product of claim 1, wherein the extracellular matrix material is selected from the group consisting, of submucosa, renal capsule membrane, durmater, pericardium, serosa, peritoneum, and basement membrane.

7. The product of claim 6, wherein the extracellular matrix material comprises submucosa.

8. The product of claim 7, wherein submucosa comprises porcine small intestine submucosa.

9. The product of claim 1, wherein said first region comprises a band that extends substantially across an entire dimension of said extracellular matrix material.

10. The product of claim 1, wherein said first region comprises a band that travels along the perimeter of the matrix material.

11. The product of claim 1, wherein said first region comprises a first elongate band and a second elongate band that intersect one another.

12. The product of claim 1, wherein said first region is in the form of a lattice.

13. The product of claim 1, wherein the medical graft product is a urethral sling.

14. The product of claim 13, wherein the sling has two arms, and wherein said second region includes at least a portion of each of said two arms.

15. The product of claim 13, wherein said first region includes a center portion of the sling.

16. The product of claim 13, wherein the first region comprises a center portion of the sling and the second region comprises at least a portion of each of two arms of the sling.

17. The product of claim 1, wherein the product is a hernia repair graft.

* * * * *